United States Patent
Ueda et al.

(10) Patent No.: US 11,358,927 B2
(45) Date of Patent: Jun. 14, 2022

(54) METHOD OF PRODUCING N,N-DISUBSTITUTED AMIDE AND CATALYST FOR PRODUCING N,N-DISUBSTITUTED AMIDE

(71) Applicant: SHOWA DENKO K.K., Tokyo (JP)

(72) Inventors: Yasuyuki Ueda, Yokohama (JP); Akira Shibuya, Kawasaki (JP); Hideo Miyata, Yokohama (JP); Hiroshi Uchida, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 72 days.

(21) Appl. No.: 17/049,792

(22) PCT Filed: Apr. 25, 2019

(86) PCT No.: PCT/JP2019/017670
§ 371 (c)(1),
(2) Date: Oct. 22, 2020

(87) PCT Pub. No.: WO2019/208705
PCT Pub. Date: Oct. 31, 2019

(65) Prior Publication Data
US 2021/0238123 A1    Aug. 5, 2021

(30) Foreign Application Priority Data

Apr. 27, 2018 (JP) .............................. JP2018-087771

(51) Int. Cl.
C07C 231/06 (2006.01)
B01J 31/02 (2006.01)

(52) U.S. Cl.
CPC ....... *C07C 231/065* (2013.01); *B01J 31/0225* (2013.01); *B01J 31/0232* (2013.01); *B01J 31/0271* (2013.01); *B01J 2231/341* (2013.01); *B01J 2531/002* (2013.01)

(58) Field of Classification Search
None
See application file for complete search history.

(56) References Cited

U.S. PATENT DOCUMENTS

| | | | | |
|---|---|---|---|---|
| 3,751,465 A | * | 8/1973 | Takahashi | C07C 231/06 564/130 |
| 3,882,175 A | * | 5/1975 | Kominami | C07C 233/00 564/125 |
| 5,041,659 A | * | 8/1991 | Cesa | C07C 231/08 564/160 |
| 5,072,024 A | * | 12/1991 | Cesa | C07C 231/065 564/204 |
| 5,099,066 A | * | 3/1992 | Cesa | C07C 231/065 554/68 |
| 5,103,055 A | * | 4/1992 | Cesa | C07C 231/065 564/204 |
| 5,118,846 A | * | 6/1992 | Cesa | C07C 231/08 564/219 |
| 6,002,010 A | * | 12/1999 | Fuchs | C07C 231/06 546/264 |

FOREIGN PATENT DOCUMENTS

| | | |
|---|---|---|
| CN | 105085341 A | 11/2015 |
| JP | 36-003967 B1 | 4/1961 |
| JP | 45-035525 B1 | 11/1970 |
| JP | 48-003813 B1 | 2/1973 |

OTHER PUBLICATIONS

Office Action dated Nov. 19, 2020 from the Intellectual Property Office of Taiwan in TW Application No. 108114472, Partial Translation.
Daniels Posevins et al., "Indium-Triflate-Catalyzed Ritter Reaction in Liquid Sulfur Dioxide", European Journal of Organic Chemistry, 2016, pp. 1414-1419, vol. 7.
Srinivasarao Yaragorla et al., "Microwave assisted, Ca(II)-catalyzed Ritter reaction for the green synthesis of amides", Tetrahedron Letters, 2014, pp. 4657-4660, vol. 55, No. 33.
Kaname Hamamoto et al., "Syntheses of N-substituted amides from nitriles and alcohols", Journal of the Chemical Society of Japan, 1959, pp. 326-328, vol. 80, No. 3.
International Search Report for PCT/JP2019/017670 dated Jul. 23, 2019 [PCT/ISA/210].

* cited by examiner

*Primary Examiner* — Amy C Bonaparte
(74) *Attorney, Agent, or Firm* — Sughrue Mion, PLLC

(57) ABSTRACT

A method of producing an N,N-disubstituted amide of the present invention is a method of reacting a nitrile with an alcohol in the presence of a catalyst, wherein the nitrile is a compound represented by $R^1CN$ ($R^1$ represents an alkyl group having 10 or less carbon atoms or an aryl group having 10 or less carbon atoms), wherein the alcohol is a compound represented by $R^2OH$ ($R^2$ represents an alkyl group having 10 or less carbon atoms), wherein the catalyst is a metal salt represented by $MX_n$ (M represents a metal cation having an oxidation number of n, X represents a monovalent anion including a substituted sulfonyl group represented by $-S(=O)_2-R^3$ ($R^3$ represents a hydrocarbon group having 10 or less carbon atoms or a group in which some or all of hydrogen atoms in the hydrocarbon group are substituted with fluorine atoms), and n represents an integer of 1 to 4), a substituent bonded to a carbon atom in a carbonyl group of the N,N-disubstituted amide is $R^1$, and two substituents bonded to nitrogen atoms in an amide group are both $R^2$.

11 Claims, No Drawings

METHOD OF PRODUCING N,N-DISUBSTITUTED AMIDE AND CATALYST FOR PRODUCING N,N-DISUBSTITUTED AMIDE

CROSS REFERENCE TO RELATED APPLICATIONS

This application is a National Stage of International Application No. PCT/JP2019/017670 filed Apr. 25, 2019, claiming priority based on Japanese Patent Application No. 2018-087771 filed Apr. 27, 2018, the content of which is incorporated herein by reference.

TECHNICAL FIELD

The present invention relates to a method of producing an N,N-disubstituted amide and a catalyst for producing an N,N-disubstituted amide.

BACKGROUND ART

N,N-disubstituted amides such as N,N-dimethylacetamide are industrially important and used as various solvents.

Regarding a method of producing an N,N-disubstituted amide, a method using a dialkylamine as a raw material is generally used. Specifically, a method of producing N,N-dimethylacetamide by reacting N,N-dimethylamine, which is an N,N-dialkylamine, with acetic acid or an acetate is used.

On the other hand, N,N-dialkylamines are generally produced by reacting ammonia with a corresponding alcohol or alkyl halide. In this reaction, since monoalkylamines and/or trialkylamines are easily produced as side products together with N,N-dialkylamines, it is necessary to separate and purify the N,N-dialkylamines after the reaction. For this reason, N,N-dialkylamines are generally expensive.

Therefore, methods of producing a corresponding N,N-disubstituted amide without using N,N-dialkylamines as a raw material have been studied (for example, refer to Patent Document 1 to Patent Document 6).

Regarding a method of producing an N,N-disubstituted amide without using an N,N-dialkylamine as a raw material, there is a method of reacting a nitrile with an alcohol in the presence of a catalyst. Regarding a catalyst and/or an accelerator that accelerates an reaction between a nitrile and an alcohol, chlorides such as $SbCl_5$, $ZnCl_2$, $SnCl_4$, and $CoCl_2$, cadmium acetate, zeolites, phosphates such as $BPO_4$, sulfates such as magnesium sulfate and aluminum sulfate, pyridine, water, and the like are used.

CITATION LIST

Patent Literature

Patent Document 1

Japanese Examined Patent Application, Second Publication No. S36-3967

Patent Document 2

Japanese Examined Patent Application, Second Publication No. S45-35525

Patent Document 3

Japanese Examined Patent Application, Second Publication No. S48-3813

Patent Document 4

U.S. Pat. No. 5,103,055

Patent Document 5

U.S. Pat. No. 5,072,024

Patent Document 6

U.S. Pat. No. 5,118,846

SUMMARY OF INVENTION

Technical Problem

However, in a production method of producing an N,N-disubstituted amide by reacting a nitrile with an alcohol in the presence of a catalyst that is used in the related art, since the efficiency of the reaction between a nitrile and an alcohol is low (the reaction rate (yield) is not high despite a high reaction temperature), an increase in reaction efficiency is required.

The present invention has been made in view of such circumstances, and an object of the present invention is to provide a method of producing an N,N-disubstituted amide and a catalyst for producing an N,N-disubstituted amide which allow an N,N-disubstituted amide to be produced with high efficiency according to a reaction between a nitrile and an alcohol.

Solution to Problem

In order to solve the above problems, the inventors conducted extensive studies regarding a catalyst that can sufficiently accelerate the reaction between a nitrile and an alcohol. As a result, it was found that it is effective to use a metal salt represented by MXn (in the formula, M represents a metal cation having an oxidation number of n, X represents a monovalent anion including at least one substituted sulfonyl group represented by $—S(═O)_2—R^3$ (in the formula, $R^3$ represents a hydrocarbon group having 10 or less carbon atoms or a group in which some or all of hydrogen atoms in the hydrocarbon group are substituted with fluorine atoms), and n represents an integer of 1 to 4) as a catalyst, and the present invention was completed.

Specifically, the present invention relates to the following items.

[1] A method of producing an N,N-disubstituted amide according to an aspect of the present invention is a method of producing an N,N-disubstituted amide by reacting a nitrile with an alcohol in the presence of a catalyst, wherein the nitrile is a compound represented by $R^1CN$ 

(in the formula, $R^1$ represents an alkyl group having 10 or less carbon atoms or an aryl group having 10 or less carbon atoms), wherein the alcohol is a compound represented by $R^2OH$ 

(in the formula, $R^2$ represents an alkyl group having 10 or less carbon atoms), wherein the catalyst includes a metal salt represented by MX$_n$ (in the formula, M represents a metal cation having an oxidation number of n, X represents a monovalent anion including at least one substituted sulfonyl group represented by —S(=O)$_2$—R$^3$ (in the formula, R$^3$ represents a hydrocarbon group having 10 or less carbon atoms or a group in which some or all of hydrogen atoms in the hydrocarbon group are substituted with fluorine atoms), and n represents an integer of 1 to 4), and wherein a substituent bonded to a carbon atom in a carbonyl group of the N,N-disubstituted amide is R$^1$, and two substituents bonded to nitrogen atoms in an amide group are both R$^2$.

[2] In the method of producing an N,N-disubstituted amide according to [1], preferably, R$^3$ is an alkyl group or a perfluoroalkyl group.

[3] In the method of producing an N,N-disubstituted amide according to [1] or [2], the catalyst may be a metal methanesulfonate.

[4] In the method of producing an N,N-disubstituted amide according to [1] or [2], the catalyst may be a metal trifluoromethanesulfonate.

[5] In the method of producing an N,N-disubstituted amide according to [1] or [2], X may be any one selected from among anions represented by the following Formulae (2) to (9):

[Chem. 1]

(2)

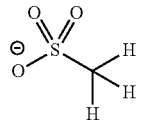

Methanesulfonate
= Mesylate = ⁻OMs (3)

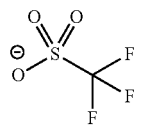

Trifluoromethanesulfonate
= Triflate = ⁻OTf (4)

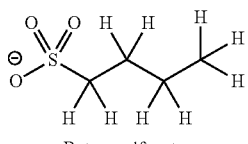

Butanesulfonate (5)

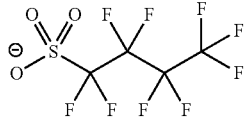

Nonafluorobutanesulfonate
= Nonaflate = ⁻ONf (6)

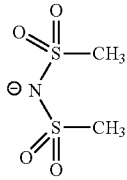

Salts of N-(methylsulfonyl)
methanesulfonamide (7)

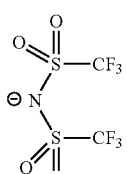

Bis(trifluoromethanesulfonyl)
imide = Triflimide = ⁻NTf$_2$ (8)

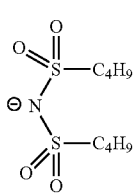

Salts of N-(butylsulfonyl)
butanesulfonamide (9)

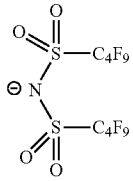

Bis(nonafluorobutanesulfonyl)
imide = Nonaflimide = ⁻NNf$_2$

[6] In the method of producing an N,N-disubstituted amide according to any one of [1] to [5], M may be any one selected from the group consisting of Zn, Cu, Sn, Al, Sc, and elements classified as lanthanoids.

[7] In the method of producing an N,N-disubstituted amide according to any one of [1] to [6], preferably, the catalyst may be used in an amount of 0.1 to 3.0 mol % with respect to a molar amount of the nitrile.

[8] In the method of producing an N,N-disubstituted amide according to any one of [1] to [7], the nitrile may be acetonitrile.

[9] In the method of producing an N,N-disubstituted amide according to any one of [1] to [8], the alcohol may be methanol.

[10] In the method of producing an N,N-disubstituted amide according to any one of [1] to [9], preferably, the reaction may be caused in an autoclave reactor under a sealed condition.

[11] In the method of producing an N,N-disubstituted amide according to any one of [1] to [10], preferably, the reaction temperature is lower than 300° C.

[12] A catalyst for producing an N,N-disubstituted amide according to one embodiment of the present invention is used when an N,N-disubstituted amide is produced by reacting a nitrile with an alcohol in the presence of a catalyst and includes a metal salt represented by MXn (in the formula, M represents a metal cation having an oxidation number of n, X represents a monovalent anion including at least one substituted sulfonyl group represented by —S(=O)$_2$—R$^3$ (in the formula, R$^3$ represents a hydrocarbon group having 10 or less carbon atoms or a group in which some or all of hydrogen atoms in the hydrocarbon group are substituted with fluorine atoms), and n represents an integer of 1 to 4).

[13] In the catalyst for producing an N,N-disubstituted amide according to [12], X may be any one selected from among anions represented by the following Formulae (2) to (9).

[Chem. 2]

(2)

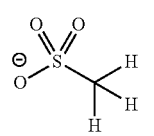

Methanesulfonate
= Mesylate = $^-$OMs (3)

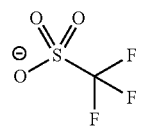

Trifluoromethanesulfonate
= Triflate = $^-$OTf (4)

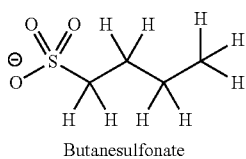

Butanesulfonate (5)

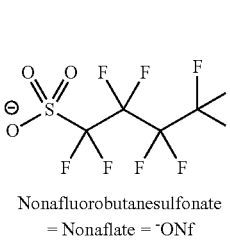

Nonafluorobutanesulfonate
= Nonaflate = $^-$ONf (6)

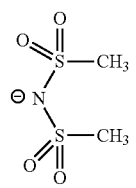

Salts of N-(methylsulfonyl)
methanesulfonamide (7)

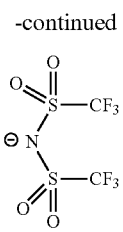

Bis(trifluoromethanesulfonyl)
imide = Triflimide = $^-$NTf$_2$ (8)

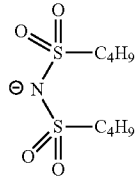

Salts of N-(butylsulfonyl)
butanesulfonamide (9)

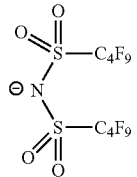

Bis(nonafluorobutanesulfonyl)
imide = Nonaflimide = $^-$NNf$_2$

[14] In the catalyst for producing an N,N-disubstituted amide according to [13], X may be an anion represented by Formula (3).

[15] In the catalyst for producing an N,N-disubstituted amide according to any one of [12] to [14], M may be any one selected from the group consisting of Zn, Cu, Sn, Al, Sc, and elements classified as lanthanoids.

[16] In the catalyst for producing an N,N-disubstituted amide according to [15], M may be any one selected from the group consisting of Zn, Nd, and Ce.

Advantageous Effects of Invention

The production method of the present invention is a method of producing an N,N-disubstituted amide by reacting a nitrile with an alcohol in the presence of a catalyst, and since a component containing a metal salt represented by MXn (in the formula, M represents a metal cation having an oxidation number of n, X represents a monovalent anion including at least one substituted sulfonyl group represented by —S(=O)$_2$—R$^3$ (in the formula, R$^3$ represents a hydrocarbon group having 10 or less carbon atoms or a group in which some or all of hydrogen atoms in the hydrocarbon group are substituted with fluorine atoms), and n represents an integer of 1 to 4) is used as the catalyst, an N,N-disubstituted amide can be produced at a high reaction rate and high efficiency.

DESCRIPTION OF EMBODIMENTS

In order to solve the above problems, the inventors have focused on the temperature for the reaction between a nitrile and an alcohol, and the amount of the catalyst, and conducted extensive studies regarding a catalyst that allows a sufficient reaction rate to be obtained.

When the temperature for the reaction between a nitrile and an alcohol is set to a high temperature exceeding 300° C., it is possible to increase the yield of the N,N-disubstituted amide. However, since both a nitrile and an alcohol used as raw materials are compounds having a low boiling point, when the reaction temperature exceeds 300° C., it is expected that the pressure in a reaction container temporarily reaches 10 MPa or more, and the compounds are in a supercritical state. Although low boiling point components are converted into a high boiling point component as the reaction progresses, and the pressure in the reaction container gradually decreases, when the reaction temperature exceeds 300° C., the reaction of synthesizing an N,N-disubstituted amide has a high risk of accident, and it is necessary to use a reaction container that has sufficient durability.

In addition, a catalyst which allows a sufficient reaction rate to be obtained with use of a small amount and which is not a chloride that degrades the durability of the reaction container is desired.

Therefore, the inventors conducted studies regarding a catalyst which allows a sufficient reaction rate to be obtained and which is not a chloride even under conditions in which the reaction temperature is set to a low temperature of lower than 300° C., and the amount of the catalyst is set to a small amount of 3.0 mol % or less with respect to the molar amount of the nitrile used as a raw material.

As a result, it was found that it is effective to use a catalyst including a metal salt represented by MXn. M represents a metal cation having an oxidation number of n, X represents a monovalent anion including at least one substituted sulfonyl group represented by $-S(=O)_2-R^3$, and n represents an integer of 1 to 4. $R^3$ represents a hydrocarbon group having 10 or less carbon atoms (preferably 1 to 8 carbon atoms, and more preferably 1 to 4 carbon atoms) or a group in which some or all of hydrogen atoms in the hydrocarbon group are substituted with fluorine atoms.

In the metal salt (MXn), the anion (X) is monovalent, and the negative charge is localized in the anion (X) due to a resonance effect of two oxygen atoms in the substituted sulfonyl group. Therefore, the positive charge is localized in the metal cation (M), the Lewis acidity of the metal cation (M) becomes strong, and high catalytic activity is obtained. By using these metal salts as catalysts, even if the reaction temperature is lower than 300° C., sufficient efficiency is achieved. For example, if the reaction temperature is set to 275° C., a nitrile can be reacted with an alcohol for a reaction time of 8 hours or shorter. In addition, since the metal salt has high catalytic activity, a sufficient reaction rate is obtained with use of a small amount. Moreover, the metal salt is not a chloride that degrades the durability of the reaction container.

The inventors completed the present invention based on such findings.

Hereinafter, a method of producing an N,N-disubstituted amide and a catalyst for producing an N,N-disubstituted amide of the present invention will be described in detail. Here, the present invention is not limited to the following embodiments.

"Method of Producing an N,N-disubstituted Amide"

In the production method of the present embodiment, a nitrile is reacted with an alcohol in the presence of a catalyst to produce an N,N-disubstituted amide represented by the following Formula (1).

[Chem. 3]

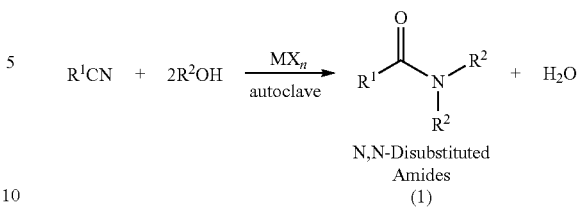

N,N-Disubstituted Amides (1)

In the production method of the present embodiment, regarding the nitrile, a compound represented by $R^1CN$ is used. In the formula, $R^1$ represents an alkyl group having 10 or less carbon atoms or an aryl group having 10 or less carbon atoms.

In addition, regarding the alcohol, a compound represented by $R^2OH$ is used. In the formula, $R^2$ represents an alkyl group having 10 or less carbon atoms.

In the N,N-disubstituted amide represented by Formula (1), the substituent bonded to a carbon atom in the carbonyl group is the above $R^1$. In the N,N-disubstituted amide represented by Formula (1), two substituents bonded to nitrogen atoms in the amide group are both the above $R^2$.

In the production method of the present embodiment, $R^1$ in the compound represented by $R^1CN$ is an alkyl group containing 10 or less carbon atoms (preferably 1 to 8 carbon atoms, and more preferably 1 to 2 carbon atoms) or an aryl group containing 10 or less carbon atoms (preferably 6 to 8 carbon atoms, and more preferably 6 to 7 carbon atoms). Regarding the alkyl group having 10 or less carbon atoms, a methyl group or an ethyl group is preferably used because it has favorable reactivity with an alcohol. Particularly, when a methyl group is used as an alkyl group having 10 or less carbon atoms (in other words, acetonitrile is used as the nitrile), this is preferable because an N,N-disubstituted acetamide, which is known to be highly useful in applications such those of a highly polar aprotic solvent, is obtained. Regarding the aryl group having 10 or less carbon atoms, a phenyl group is preferably used because of ease of availability and inexpensiveness.

In the production method of the present embodiment, in the compound represented by $R^2OH$, $R^2$ represents an alkyl group having 10 or less carbon atoms (preferably 1 to 8 carbon atoms, and more preferably 1 to 3 carbon atoms). Regarding the alkyl group having 10 or less carbon atoms, a methyl group, an ethyl group, or an n-propyl group is preferably used, and particularly, it is more preferable to use a methyl group (in other words, methanol is used as the alcohol) because side products (alkenes and the like according to intramolecular dehydration of alcohols) are unlikely to be generated, and an N,N-dimethylamide, which is known to be highly useful in applications such as those of a highly polar aprotic solvent, is obtained.

In the production method of the present embodiment, $R^1$ in the compound represented by $R^1CN$ and $R^2$ in the compound represented by $R^2OH$ may be the same as or different from each other.

A desired compound synthesized by the production method of the present embodiment is an N,N-disubstituted amide represented by Formula (1). $R^1$ in Formula (1) is $R^1$ in the compound represented by $R^1CN$ used as a nitrile. $R^2$ in Formula (1) is $R^2$ in the compound represented by $R^2OH$ used as an alcohol.

In the N,N-disubstituted amide represented by Formula (1), preferably, $R^1$ is any one selected from the group consisting of a methyl group, an ethyl group, and a phenyl group, and $R^2$ is any one selected from the group consisting of a methyl group, an ethyl group, and an n-propyl group. Particularly, an N,N-dimethylacetamide in which $R^1$ and $R^2$ are a methyl group is preferable. When the N,N-disubstituted amide represented by Formula (1) is an N,N-dimethylacetamide, it can be efficiently synthesized at a higher reaction rate.

In the production method of the present embodiment, the reaction between a nitrile and an alcohol is preferably performed in a closed autoclave reaction container. This allows the reaction to proceed stably.

When a nitrile is reacted with an alcohol in the sealed autoclave reactor, if oxygen gas is contained in the atmosphere in the reaction container, the alcohol is oxidized to produce an aldehyde, the aldehyde additionally reacting with the alcohol to form an acetal as a side product in some cases. Therefore, the atmosphere in the reaction container is preferably an inert atmosphere of nitrogen gas, argon gas or the like. Here, when a sealed container contains starting materials under an air atmosphere with an atmospheric pressure, the volume of air contained in the sealed container is reduced, and the amount of oxygen gas in the sealed container is set to be much smaller than the amount of the alcohol (about 1% or less of the amount of the alcohol), it is thereby possible to minimize the yield of an acetal as a side-product.

The internal pressure of the reaction container during the reaction is preferably less than 10 MPa and more preferably 8 MPa or less in all processes from the start to the end of the reaction. In addition, the internal pressure in the reaction container during the reaction is preferably an atmospheric pressure (0.1 MPa) or more.

The temperature for the reaction between a nitrile and an alcohol may be a temperature which is lower than 300° C. and within a range in which the reaction between a nitrile and an alcohol proceeds and is preferably 280° C. or lower. When the reaction temperature is lower, the internal pressure in the reaction container during the reaction is lower, and thus the safety of the synthesis reaction of the N,N-disubstituted amide is improved and the damage on the reaction container is reduced. However, since the reaction rate becomes lower as the reaction temperature becomes lower, the reaction temperature is preferably 100° C. or higher, more preferably 150° C. or higher, and still more preferably 180° C. or higher. The time for the reaction between a nitrile and an alcohol is preferably in a range of 2 to 24 hours, more preferably in a range of 3 to 12 hours, and still more preferably in a range of 4 to 8 hours.

"Catalyst for Producing an N,N-disubstituted Amide"

In the method of producing an N,N-disubstituted amide of the present embodiment, a catalyst for producing an N,N-disubstituted amide (hereinafter sometimes is simply referred to as a "catalyst") of the present embodiment shown below is used.

The catalyst of the present embodiment is used when an N,N-disubstituted amide is produced when a nitrile is reacted with an alcohol in the presence of a catalyst.

The catalyst of the present embodiment includes a metal salt represented by MXn. In the formula, M represents a metal cation having an oxidation number of n, X represents a monovalent anion including at least one substituted sulfonyl group represented by $-S(=O)_2-R^3$, and n represents an integer of 1 to 4. In the formula, $R^3$ represents a hydrocarbon group having 10 or less carbon atoms or a group in which some or all of hydrogen atoms in the hydrocarbon group are substituted with fluorine atoms.

The metal salt itself represented by MXn can be used alone as a catalyst, or that obtained by supporting a metal salt represented by MXn on a carrier that does not adversely affect the reaction may be used as a catalyst. In order to cause a reaction in a uniform reaction system, a metal salt represented by MXn that is soluble in a nitrile and an alcohol is preferably used alone as a catalyst.

M constituting the metal salt represented by MXn is a metal cation having an oxidation number n of 1 to 4, and is preferably a metal cation having an oxidation number n of 2 to 4. Specifically, examples of M in the metal salt represented by MXn include Zn, Cu, Sn, Al, Sc, elements classified as lanthanoids (La, Ce, Pr, Nd, Pm, Sm, Eu, Gd, Tb, Dy, Ho, Er, Tm, Yb, Lu), and Ag. Among these, any one selected from the group consisting of Zn, Nd, and Ce is preferably used. In this case, a catalyst with a higher reaction rate is obtained. In addition, it is preferable that M is not cadmium from the viewpoint of toxicity reduction.

X constituting the metal salt represented by MXn represents a monovalent anion including at least one substituted sulfonyl group represented by $-S(=O)_2-R^3$.

In the formula, $R^3$ represents a hydrocarbon group having 10 or less carbon atoms or a group in which some or all of hydrogen atoms constituting the hydrocarbon group are substituted with fluorine atoms.

The number of substituted sulfonyl groups contained in X is preferably 1 or 2, and more preferably 1.

$R^3$ contained in the substituted sulfonyl group is preferably an alkyl group or a perfluoroalkyl group, and a perfluoroalkyl group is more preferable because the Lewis acidity of the metal cation becomes strong, and high catalytic activity is obtained.

Specifically, X constituting the metal salt represented by MXn is preferably an anion represented by the following Formulae (2) to (9). When X is an anion represented by Formulae (2) to (9), the metal salt represented by MXn is preferable because it is soluble in a nitrile and an alcohol at room temperature and acts as a homogeneous catalyst.

Among these, X constituting the metal salt represented by MXn is more preferably an anion selected from among a mesylate anion represented by Formula (2) (in other words, the catalyst is a metal methanesulfonate), a triflate anion represented by Formula (3) (in other words, the catalyst is a metal trifluoromethanesulfonate) and a triflimide anion represented by Formula (7) (in other words, the catalyst is a metal bis(trifluoromethanesulfonyl)imide salt), and particularly preferably an anion represented by Formula (3) or (7). When X constituting the metal salt represented by MXn is an anion represented by Formula (3) or (7), a catalyst with a higher reaction rate is obtained.

[Chem. 4]

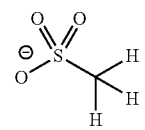

(2)

Methanesulfonate
= Mesylate = ⁻OMs (3)

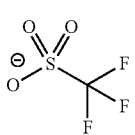

Trifluoromethanesulfonate
= Triflate = ⁻OTf (4)

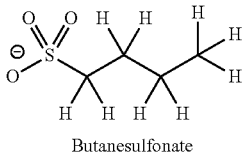

Butanesulfonate (5)

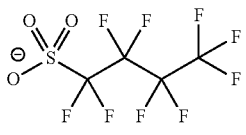

Nonafluorobutanesulfonate
= Nonaflate = ⁻ONf (6)

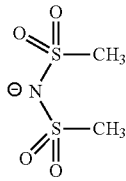

Salts of N-(methylsulfonyl)
methanesulfonamide (7)

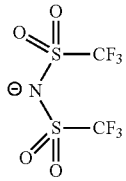

Bis(trifluoromethanesulfonyl)
imide = Triflimide = ⁻NTf$_2$ (8)

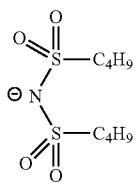

Salts of N-(butylsulfonyl)
butanesulfonamide (9)

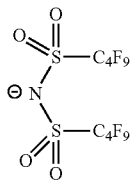

Bis(nonafluorobutanesulfonyl)
imide = Nonaflimide = ⁻NNf$_2$

On the other hand, for example, when BPO$_4$ is used as a catalyst, BPO$_4$ does not dissolve in a starting material at room temperature but dissolves in the side product N-monosubstituted amide. Therefore, it is thought that BPO$_4$ dissolves in the N-monosubstituted amide during the reaction and acts as a homogeneous catalyst. Therefore, when BPO$_4$ is used as a catalyst, the reaction path may vary due to a slight difference in experimental conditions such as a time at which the catalyst starts to act as a homogeneous catalyst, and there is concern regarding reproducibility.

The amount of the catalyst used is preferably 0.1 to 3.0 mol % and more preferably 0.5 to 1.0 mol % with respect to the molar amount of the nitrile. When the amount of the catalyst used is 0.1 mol % or more with respect to the molar amount of the nitrile, it is possible to effectively improve the reactivity. In addition, when the amount of the catalyst used is 3.0 mol % or less with respect to the molar amount of the nitrile, separation of the catalyst itself from the desired compound is less complicated, side reactions can be minimized, and a catalyst cost can be reduced.

EXAMPLES

The present invention will be described below in more detail with reference to examples and comparative examples. Here, the present invention is not limited to the following examples. Here, the pressure in the following examples and comparative examples is a gauge pressure.

Example 1

Acetonitrile (11 g, 0.26 mol), methanol (16 g, 0.52 mol), and zinc (II) trifluoromethanesulfonate (0.8 g, 2 mmol) as a catalyst were put into a 100 mL autoclave reactor (commercially available from Nitto Kouatsu, allowable maximum internal temperature of 300° C., having a 10 MPa safety valve attached) made of stainless steel (SUS316) to prepare a solution, and the autoclave reactor was sealed under an air atmosphere with an atmospheric pressure.

In order to check whether there was leakage, nitrogen gas at about 8 MPa was supplied using a nitrogen cylinder into the closed autoclave reactor, and it was confirmed that there was no leakage. Then, the valve attached to the autoclave reaction container was opened, the inside of the autoclave reaction container was set to have a nitrogen gas atmosphere with atmospheric pressure, and the valve was then closed, and put under a sealed condition again.

The content in the autoclave reactor was stirred using stirring blades, the autoclave reactor was heated in an electric furnace for 4 hours while performing measurement using a thermometer so that the internal temperature was maintained at 275° C., and acetonitrile was reacted with methanol. The internal pressure of the autoclave reactor during the reaction increased to 7.20 [MPa] and then gradually decreased and was 3.30 [MPa] while the temperature was maintained at 275° C. for 4 hours. Then, the autoclave reactor and its content were cooled to room temperature, the valve attached to the autoclave reaction container was opened in the draft chamber, a gaseous product that was not dissolved in the liquid reaction mixture was released and thus the residual pressure (0.20 MPa, weight reduction 1.0 g) was removed. Then, the autoclave reaction container was opened under an air atmosphere and a reaction mixture (26.1 g) as a dark brown liquid was obtained.

The compound composition in the reaction mixture was analyzed using gas chromatography (GC). As a result, in addition to the desired component N,N-dimethylacetamide, acetamide, N-methylacetamide, acetic acid, methyl acetate, dimethylamine, dimethyl ether, methylamine, and ammonia were produced as side products.

The yield of the desired component N,N-dimethylacetamide in the reaction mixture and conversion rates of acetonitrile and methanol as raw materials were obtained by the following method. The results are shown in Table 1.

(Gas Chromatography (GC) Yield)

First, a calibration curve of the desired compound was obtained according to the following method. A commercial product (N,N-dimethylacetamide: commercially available from FUJIFILM Wako Pure Chemical Corporation, for ultra-dehydration and organic synthesis) of a desired compound was diluted using a mixed solution in which acetonitrile and methanol were mixed at a molar ratio of 1:2 (MeCN:MeOH), and three or more desired samples having different concentrations were prepared. The samples were analyzed using gas chromatography (GC) and a calibration curve was obtained from the obtained peak areas.

Next, the yield was calculated using the calibration curve obtained by the above method according to the following method. The reaction mixture was analyzed using gas chromatography (GC), a peak area of a desired component in the reaction mixture was obtained, and based on the calibration curve obtained by the above method and the collected reaction mixture mass, the amount of the desired component in the reaction mixture was calculated, and the number of moles thereof was obtained. Then, the ratio of the number of moles of the desired component in the reaction mixture to the number of moles of acetonitrile used as a raw material was obtained to calculate a yield.

(Conversion Rate)

A calibration curve was obtained by the following method, and based on the results of analysis using gas chromatography (GC), the amounts of acetonitrile and methanol in the reaction mixture were obtained, and the conversion rates were calculated by performing subtraction from an amount used as a starting material.

Three or more types of samples which were a mixed solution containing acetonitrile and methanol and which had a different concentration of acetonitrile in a range of 5 to 20 mass % were prepared. The samples were analyzed using gas chromatography (GC), and a calibration curve of acetonitrile was obtained from the obtained peak areas.

On the other hand, three or more types of samples which were a mixed solution containing acetonitrile and methanol and which had a different concentration of methanol in a range of 5 to 20 mass % were prepared. The samples were analyzed using gas chromatography (GC), and a calibration curve of methanol was obtained from the obtained peak areas.

Examples 2 to 11 and Comparative Examples 1 to 8

Reaction mixtures of Examples 2 to 9, 1 and Comparative Examples 1 to 8 were obtained in the same manner as in Example 1 except that catalysts shown in Table 1 were used in amounts of the catalysts shown in Table 1.

In addition, a reaction mixture of Example 10 was obtained in the same manner as in Example 1 except that silver methanesulfonate (AgOMs, commercially available from Aldrich) and 0.5 equivalent of $ZnCl_2$ (commercially available from Wako Pure Chemical Industries, Ltd.) were added to a mixed solution in which nitrile and alcohol at a substance amount (molar) ratio of 1:2 (MeCN:MeOH) and mixed, a solution obtained by removing hardly soluble precipitate (AgCl) as a mixture of starting materials was put into the reaction container, and the container was closed. In Example 10, zinc methanesulfonate ($(Zn(OMs)_2)$) which was a compound contained in the starting material produced by the reaction between silver methanesulfonate and $ZnCl_2$ and functioned as a catalyst was used as the catalyst.

The compound compositions in the reaction mixtures of Examples 2 to 11 and Comparative Examples 1 to 8 were analyzed using gas chromatography (GC). As a result, in all of Examples 2 to 11 and Comparative Examples 1 to 8, in addition to the desired component N,N-dimethylacetamide, acetamide, N-methylacetamide, acetic acid, methyl acetate, dimethylamine, dimethyl ether, methylamine, and ammonia were produced as side products.

The yields of the desired component N,N-dimethylacetamides in the reaction mixtures of Examples 2 to 11 and Comparative Examples 1 to 8 obtained in this manner and the conversion rates of acetonitrile and methanol as raw materials were obtained in the same manner as in Example 1. The results are shown in Table 1.

In addition, Table 1 shows the type of catalysts used in Examples 1 to 11 and Comparative Examples 1 to 8, the supply source of the catalyst, and the amount of the catalyst (the amount used with respect to the molar amount of the nitrile). In Table 1, "MeCN" indicates acetonitrile, and "MeOH" indicates methanol. In addition, "OTf" indicates a triflate anion represented by Formula (3), "OMs" indicates a mesylate anion represented by Formula (2), and "$NTf_2$" indicates a triflimide anion represented by Formula (5). In addition, "SAPO" indicates silicoaluminophosphate, and "$Zn(OAc)_2$" indicates zinc acetate.

TABLE 1

| | Type of catalyst | Supply source | Amount of catalyst [mol %] | MeCN conversion rate [%] | MeOH conversion rate [%] | Yield of N,N-dimethylacetamide [%] |
|---|---|---|---|---|---|---|
| Example 1 | $Zn(OTf)_2$ | Tokyo Chemical Industry | 0.8 | 83 | 75 | 21 |
| Example 2 | $Zn(OTf)_2$ | Tokyo Chemical Industry | 3.0 | 89 | 73 | 23 |
| Example 3 | $Cu(OTf)_2$ | Tokyo Chemical Industry | 0.8 | 85 | 78 | 9.5 |
| Example 4 | $Sn(OTf)_2$ | Tokyo Chemical Industry | 0.7 | 88 | 81 | 13 |
| Example 5 | $Al(OTf)_3$ | Aldrich | 0.8 | 88 | 81 | 14 |

TABLE 1-continued

| | Type of catalyst | Supply source | Amount of catalyst [mol %] | MeCN conversion rate [%] | MeOH conversion rate [%] | Yield of N,N-dimethylacetamide [%] |
|---|---|---|---|---|---|---|
| Example 6 | $Sc(OTf)_3$ | Tokyo Chemical Industry | 0.6 | 90 | 87 | 13 |
| Example 7 | $La(OTf)_3$ | Tokyo Chemical Industry | 0.8 | 90 | 84 | 15 |
| Example 8 | $Nd(OTf)_3$ | Tokyo Chemical Industry | 0.8 | 89 | 82 | 23 |
| Example 9 | $Ce(OTf)_4$ | Alfa Aesar | 0.8 | 84 | 79 | 22 |
| Example 10 | $Zn(OM_S)_2$ | — | 0.8 | 78 | 64 | 5.5 |
| Example 11 | $Zn(NTf_2)_2$ | Tokyo Chemical Industry | 0.6 | 86 | 73 | 13 |
| Comparative Example 1 | $BPO_4$ | Alfa Aesar | 0.8 | 79 | 68 | 2.1 |
| Comparative Example 2 | $BPO_4$ | Yoneyama Chemical Industry Co., Ltd | 0.8 | 68 | 61 | 1.6 |
| Comparative Example 3 | $BPO_4$ | Yoneyama Chemical Industry Co., Ltd | 8.0 | 90 | Not determined | 15 |
| Comparative Example 4 | $AlPO_4$ | Alfa Aesar | 6.6 | 17 | 10 | 0.15 |
| Comparative Example 5 | SAPO | ACS Materials | 2.0 | 7.4 | 1.8 | 0.013 |
| Comparative Example 6 | $ZnSO_4$ | Junsei Chemical Co., Ltd. | 0.8 | 14 | 3.9 | 0.0089 |
| Comparative Example 7 | $Zn(OA_C)_2$ | FUJIFILM Wako Pure Chemical Corporation | 0.8 | 14 | 7.6 | 0.0054 |
| Comparative Example 8 | $H_2O$ | Distilled water | 1.0 equivalent | 19 | 7.2 | 0.011 |

As shown in Table 1, in Examples 1, 3, 5, and 7 to 10 using the metal salt represented by MXn, which was the catalyst of the present invention, it was confirmed that the yield of the N,N-dimethylacetamide was higher and the catalytic activity was higher than those in Comparative Examples 1, 2, 6, and 7 in which the amount of the catalyst (molar amount) was the same as the above examples and Comparative Examples 4, 5, and 8 in which the amount of the catalyst (molar amount) was larger than that of the above example. It was suggested that the catalyst of the present invention containing a metal salt including the anion was effective compared to the catalyst including an acetate ion as an anion disclosed in Patent Documents 2 and 5 and the catalyst including a phosphate ion or a sulfate ion as an anion disclosed in Patent Document 5.

In addition, it was confirmed that, in Examples 4, 6, and 11, the yield of the N,N-dimethylacetamide was higher and the catalytic activity was higher than those in Comparative Examples 1, 2, and 4 to 8 in which the amount of the catalyst was larger than that of the above example.

In addition, it was confirmed that, in Example 2, the yield of the N,N-dimethylacetamide was higher and the catalytic activity was higher than those in Comparative Examples 3 and 4 in which the amount of the catalyst was larger than that of the above example.

In addition, in Comparative Example 3, the same catalyst as in Comparative Example 2 was used in an amount of 8 mol %, but the yield of the N,N-dimethylacetamide was about the same as in Example 7 in which the amount of the catalyst was 1/10, and the catalytic activity was low.

Accordingly, it was found that the catalysts used in Examples 1 to 11 had high catalytic activity even if the reaction temperature was low at 275° C. In addition, it was found that, since the catalysts used in Examples 1 to 11 had high catalytic activity, the reaction was caused in a short time of about 4 hours even with use of a small amount of 0.8 mol % or less, and the effect of increasing the reaction rate was obtained.

Examples 13 to 16

The reaction mixtures of Examples 13 to 16 were obtained in the same manner as in Example 1 except that a nitrile represented by $R^1CN$ (in the formula, $R^1$ is as shown in Table 2) was used in place of acetonitrile, an alcohol represented by $R^2OH$ (in the formula, $R^2$ is as shown in Table 2) was used in place of methanol, the nitrile and the alcohol were mixed at a substance amount (molar) ratio of 1:2 (nitrile:alcohol), and the reaction time shown in Table 2 was set.

Examples 12 and 17

The reaction mixture of Example 12 was obtained in the same manner as in Example 1 except that the reaction temperature was set to 250° C. and the reaction time shown in Table 2 was set.

In addition, the reaction mixture of Example 17 was obtained in the same manner as in Example 16 except that the reaction temperature was set to 250° C. and the reaction time shown in Table 2 was set.

The yield of the N,N-disubstituted amide which was a desired component in the reaction mixture in Example 12 obtained in this manner was obtained in the same manner as in Example 1.

In addition, the yields of the N,N-disubstituted amides which were a desired component in the reaction mixtures of Examples 13 to 17 were obtained by the following method.

The reaction mixtures were analyzed using gas chromatography (GC). A ratio of the peak area of the desired component to all peak areas was calculated and used as the yield of the N,N-disubstituted amide.

In addition, the conversion rates of acetonitrile and methanol among raw materials of Examples 12 to 17 were obtained in the same manner as in Example 1. The results are shown in Table 2.

In Table 2, "Me" indicates a methyl group, "Et" indicates an ethyl group, "Ph" indicates a phenyl group, and "n-Pr" indicates an n-propyl group.

In addition, for ease of comparison, Table 2 also shows Example 1 shown in Table 1. In addition, the GC yield in Example 1 was the same as in Table 1.

TABLE 2

| | $R^1$ | $R^2$ | Reaction temperature [° C.] | Reaction time [h] | $R^1CN$ conversion rate [%] | $R^2OH$ conversion rate [%] | Yield of N,N-disubstituted amide [%] (value in parentheses is ratio [%] of GC peak area) |
|---|---|---|---|---|---|---|---|
| Example 1 | Me | Me | 275 | 4.0 | 83 | 75 | 21 |
| Example 12 | Me | Me | 250 | 8.0 | 82 | 63 | 9.5 |
| Example 13 | Me | Et | 275 | 6.0 | 67 | — | (2.5) |
| Example 14 | Me | n-Pr | 275 | 7.0 | 61 | — | (1.1) |
| Example 15 | Et | Me | 275 | 4.0 | — | 78 | (17) |
| Example 16 | Ph | Me | 275 | 4.0 | — | 79 | (13) |
| Example 17 | Ph | Me | 250 | 6.0 | — | 69 | (3.3) |

As shown in Table 2, it was found that, in zinc(II) trifluoromethanesulfonate which was a catalyst used in Examples 1, and 12 to 17, when $R^1$ was any one selected from the group consisting of a methyl group, an ethyl group, and a phenyl group and $R^2$ was any one selected from the group consisting of a methyl group, an ethyl group, and an n-propyl group, even if the reaction temperature was low at 275° C. (in Examples 12 and 17, 250° C.), the catalytic activity was obtained. In addition, it was found that the catalyst had an effect of increasing a reaction rate even with use of a small amount of 0.8 mol %.

Particularly, in the reaction (Examples 1 and 12) in which a dimethylacetamide in which $R^1$ and $R^2$ were a methyl group was synthesized, it was confirmed that the reaction acceleration effect of the catalyst was significant and synthesis was performed with high efficiency.

What is claimed is:

1. A method of producing an N,N-disubstituted amide by reacting a nitrile with an alcohol in the presence of a catalyst,
   wherein the nitrile is a compound represented by $R^1CN$ wherein in the formula, $R^1$ represents an alkyl group having 10 or less carbon atoms or an aryl group having 10 or less carbon atoms,
   wherein the alcohol is a compound represented by $R^2OH$ wherein in the formula, $R^2$ represents an alkyl group having 10 or less carbon atoms,
   wherein the catalyst includes a metal salt represented by MXn wherein in the formula, M represents a metal cation having an oxidation number of n, X represents a monovalent anion including at least one substituted sulfonyl group represented by —S(=O)$_2$—R$^3$, wherein in the formula R$^3$ represents a hydrocarbon group having 10 or less carbon atoms or a group in which some or all of the hydrogen atoms in the hydrocarbon group are substituted with fluorine atoms, and n represents an integer of 1 to 4, and
   wherein a substituent bonded to a carbon atom in a carbonyl group of the N,N-disubstituted amide is $R^1$, and two substituents bonded to nitrogen atoms in an amide group are both $R^2$.

2. The method of producing an N,N-disubstituted amide according to claim 1,
   wherein $R^3$ is an alkyl group or a perfluoroalkyl group.

3. The method of producing an N,N-disubstituted amide according to claim 1,
   wherein the catalyst is a metal methanesulfonate.

4. The method of producing an N,N-disubstituted amide according to claim 1,
   wherein the catalyst is a metal trifluoromethanesulfonate.

5. The method of producing an N,N-disubstituted amide according to claim 1,
   wherein X is any one selected from among anions represented by the following Formulae (2) to (9):

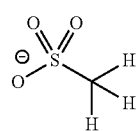

(2)

Methanesulfonate = Mesylate = ⁻OMs

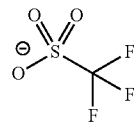

(3)

Trifluoromethanesulfonate = Triflate = ⁻OTf (4)

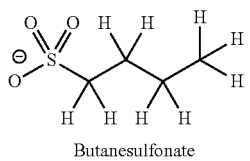

Butanesulfonate (5)

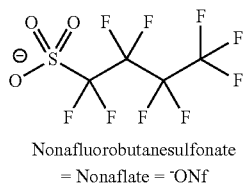

Nonafluorobutanesulfonate
= Nonaflate = ⁻ONf (6)

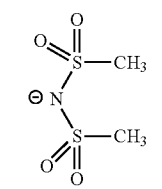

N-(methylsulfonyl)
methanesulfonamide (7)

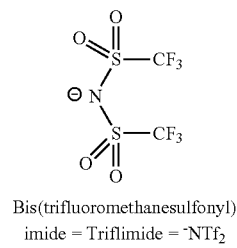

Bis(trifluoromethanesulfonyl)
imide = Triflimide = ⁻NTf$_2$ (8)

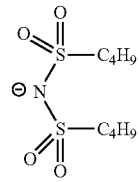

N-(butylsulfonyl)
butanesulfonamide (9)

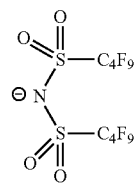

Bis(nonafluorobutanesulfonyl)
imide = Nonaflimide = ⁻NNf$_2$

6. The method of producing an N,N-disubstituted amide according to claim 1,
wherein M is any one selected from the group consisting of Zn, Cu, Sn, Al, Sc, and elements classified as lanthanoids.

7. The method of producing an N,N-disubstituted amide according to claim 1,
wherein the catalyst is used in an amount of 0.1 to 3.0 mol % with respect to a molar amount of the nitrile.

8. The method of producing an N,N-disubstituted amide according to claim 1,
wherein the nitrile is acetonitrile.

9. The method of producing an N,N-disubstituted amide according to claim 1,
wherein the alcohol is methanol.

10. The method of producing an N,N-disubstituted amide according to claim 1,
wherein the reaction is caused in an autoclave reactor under a sealed condition.

11. The method of producing an N,N-disubstituted amide according to claim 1,
wherein the reaction temperature is lower than 300° C.

* * * * *